(12) United States Patent
Yiu

(10) Patent No.: US 10,308,575 B2
(45) Date of Patent: Jun. 4, 2019

(54) METHANOL PROCESS

(71) Applicant: JOHNSON MATTHEY DAVY TECHHNOLOGIES LIMITED, London (GB)

(72) Inventor: Kar Chi Yiu, London (GB)

(73) Assignee: Johnson Matthey Davy Technologies Limited, London, England (GB)

( * ) Notice: Subject to any disclaimer, the term of this patent is extended or adjusted under 35 U.S.C. 154(b) by 0 days.

(21) Appl. No.: 16/067,419

(22) PCT Filed: Dec. 16, 2016

(86) PCT No.: PCT/GB2016/053960
§ 371 (c)(1),
(2) Date: Jun. 29, 2018

(87) PCT Pub. No.: WO2017/121981
PCT Pub. Date: Jul. 20, 2017

(65) Prior Publication Data
US 2019/0016655 A1     Jan. 17, 2019

(30) Foreign Application Priority Data
Jan. 15, 2016 (GB) .................................. 1600794.0

(51) Int. Cl.
*B01D 3/14*     (2006.01)
*C01B 3/50*     (2006.01)
(Continued)

(52) U.S. Cl.
CPC .......... *C07C 29/1516* (2013.01); *B01D 3/143* (2013.01); *B01J 23/72* (2013.01);
(Continued)

(58) Field of Classification Search
CPC ..... C07C 31/04; C07C 29/152; C07C 29/154; B01J 2523/31; B01J 2523/27;
(Continued)

(56) References Cited

U.S. PATENT DOCUMENTS 3,458,289 A     7/1969     King et al.
3,475,136 A     10/1969     Eschenbrenner et al.
(Continued)

FOREIGN PATENT DOCUMENTS

DE     3518362 A1     11/1986
WO     WO 2012/146904 A1     11/2012
(Continued)

OTHER PUBLICATIONS

PCT/GB2016/053960 International Search Report and Written Opinion dated Feb. 23, 2017.
(Continued)

*Primary Examiner* — Jafar F Parsa
(74) *Attorney, Agent, or Firm* — BakerHostetler

(57) ABSTRACT

A process is described for the synthesis of methanol comprising the steps of: (i) passing a first synthesis gas mixture comprising a make-up gas through a first synthesis reactor containing a cooled methanol synthesis catalyst to form a first product gas stream, (ii) recovering methanol from the first product gas stream thereby forming a first methanol-depleted gas mixture, (iii) combining the first methanol-depleted gas mixture with a loop recycle gas stream to form a second synthesis gas mixture, (iv) passing the second synthesis gas mixture through a second synthesis reactor containing a cooled methanol synthesis catalyst to form a second product gas stream, (v) recovering methanol from the second product gas stream thereby forming a second methanol-depleted gas mixture, and (vi) using at least part of the second methanol-depleted gas mixture as the loop recycle
(Continued)

gas stream, wherein the first synthesis reactor has a higher heat transfer per cubic meter of catalyst than the second synthesis reactor, none of the loop recycle gas stream is fed to the first synthesis gas mixture and the recycle ratio of the loop recycle gas stream to form the second synthesis gas mixture is in the range 1.1:1 to 6:1.

16 Claims, 1 Drawing Sheet

(51) Int. Cl.
| | |
|---|---|
| *B01J 23/72* | (2006.01) |
| *C07C 31/04* | (2006.01) |
| *C07C 29/151* | (2006.01) |
| *C07C 29/152* | (2006.01) |
| *C07C 29/154* | (2006.01) |

(52) U.S. Cl.
CPC ............ *C01B 3/506* (2013.01); *C07C 29/152* (2013.01); *C07C 29/154* (2013.01); *C07C 31/04* (2013.01); *B01D 2256/16* (2013.01); *B01D 2257/70* (2013.01); *B01J 2203/06* (2013.01); *B01J 2523/17* (2013.01); *B01J 2523/27* (2013.01); *B01J 2523/31* (2013.01); *C01B 2203/0216* (2013.01); *C01B 2203/0283* (2013.01); *C01B 2203/061* (2013.01); *Y02P 20/132* (2015.11)

(58) Field of Classification Search
CPC .. B01J 2523/17; B01J 2523/06; Y02P 20/132; C01B 3/506; C01B 2203/0216; C01B 2203/061
See application file for complete search history.

(56) References Cited

U.S. PATENT DOCUMENTS

| | | |
|---|---|---|
| 4,321,234 A | 3/1982 | Ohsaki et al. |
| 4,411,877 A | 10/1983 | Notman et al. |
| 5,631,302 A | 5/1997 | Konig et al. |
| 5,827,901 A | 10/1998 | Konig et al. |
| 7,790,775 B2 | 9/2010 | Early |
| 8,536,235 B2 | 9/2013 | Fitzpatrick |
| 8,629,191 B2 | 1/2014 | Kopetsch et al. |
| 2011/0065966 A1 | 3/2011 | Mueller et al. |
| 2014/0031438 A1 | 1/2014 | Hackel et al. |

FOREIGN PATENT DOCUMENTS

| | | |
|---|---|---|
| WO | WO 2014/012601 A1 | 1/2014 |
| WO | WO 2014/206635 A1 | 12/2014 |

OTHER PUBLICATIONS

GB1600794.0 Search Report under Section 17(5) dated Nov. 10, 2016.
GB1621445.4 Combined Search and Examination Report under Sections 17 and 18(3) dated Sep. 25, 2017.
PCT/GB2016/053960 Third Party Observations dated May 11, 2018.
Landalv, et al., Environmental Progress & Sustainable Energy, vol. 33, No. 3, pp. 744-750, first published May 19, 2014.
Johnson Matthey Davy Technologies, Oct. 2015, "Synthesis", davyprotech.com. Available from: https://web.archive/web20151023025714/http://davyprotech.com/what-we-do-licensed-processes-and-core-technologies/core-technologies/synthesis/specification/ [Archived entry date—Oct. 23, 2015].
S.Nielsen et al., Topsoe Ammonia & Methanol Co-Production, Haldor Topsoe, pp. 1-18, Publication 2012.

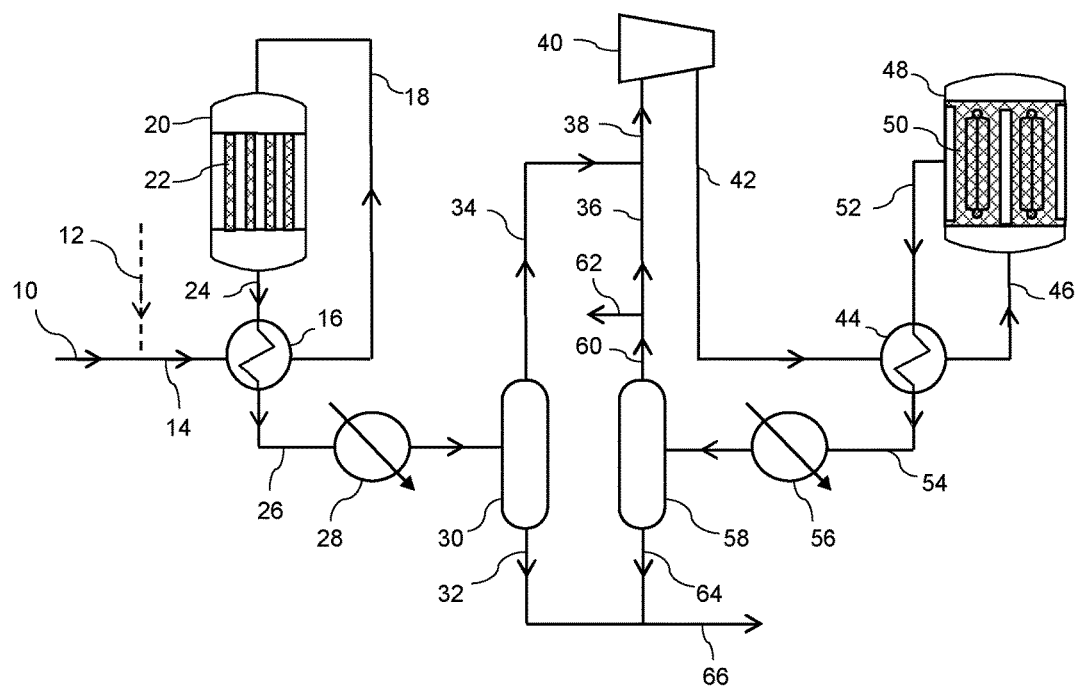

METHANOL PROCESS

CROSS-REFERENCE TO RELATED APPLICATIONS

This application is the National Stage of International Patent Application No. PCT/GB2016/053960, filed Dec. 16, 2016, which claims priority from Great Britain Patent Application No. 1600794.0, filed Jan. 15, 2016, the disclosures of each of which are incorporated herein by reference in their entireties for any and all purposes.

This invention relates to a process for synthesising methanol.

Methanol synthesis is generally performed by passing a synthesis gas comprising hydrogen, carbon oxides and any inert gases at an elevated temperature and pressure through one or more beds of a methanol synthesis catalyst, which is often a copper-containing composition. Methanol is generally recovered by cooling the product gas stream to below the dew point of the methanol and separating off the product as a liquid. The crude methanol is typically purified by distillation. The process is often operated in a loop: thus the remaining unreacted gas stream is usually recycled to the synthesis reactor as part of the synthesis gas via a circulator. Fresh synthesis gas, termed make-up gas, is added to the recycled unreacted gas to form the synthesis gas stream. A purge stream is often taken from the circulating gas stream to avoid the build-up of inert gasses.

The process may be operated using two synthesis reactors each containing a bed of methanol synthesis catalyst.

U.S. Pat. No. 7,790,775 discloses a process for use in equilibrium exothermic gas phase reactions comprising the steps of (a) providing a recycle stream with the addition of make-up gas, to form a feed gas stream; (b) heating the feed gas stream; (c) passing the heated feed gas stream to a first reactor containing a catalyst for the exothermic gas phase reactions at conditions suitable for the reaction; (d) removing a product stream comprising product and unreacted gases from the first reactor; (e) cooling and partially condensing the product stream to form a gas phase and a liquid phase; (f) separating the liquid phase containing the desired product from the product stream and removing said liquid phase; (g) separating the gas phase from the product stream to form a gas stream; (h) optionally mixing the gas stream from the product stream with additional make-up gas; (i) heating the gas stream; (j) passing the heated gas stream to a final reactor containing a catalyst for the exothermic gas phase reactions at conditions suitable for the reaction; (k) removing a final product stream comprising product and unreacted gases from the final reactor; (l) cooling and partially condensing the final product stream to form a final gas phase and a final liquid phase; (m) separating the final liquid phase containing the desired product from the final product stream and removing said final liquid phase; and (n) separating the gas phase from the final product stream and recycling the gas to step (a); and in which the gas stream from step (g) is compressed prior to heating in step (i).

U.S. Pat. No. 8,536,235 discloses a process for the synthesis of methanol comprising the steps of: (a) passing a synthesis gas mixture comprising a loop gas and a make-up gas through a first synthesis reactor containing a methanol synthesis catalyst, said reactor cooled by boiling water under pressure, to form a mixed gas containing methanol, (b) cooling the mixed gas containing methanol, (c) passing said cooled mixed gas containing methanol through a second synthesis reactor containing a methanol synthesis catalyst in which further methanol is synthesised to form a product gas stream, (d) cooling said product gas to condense methanol, (e) recovering said methanol and returning unreacted gas as the loop gas to said first synthesis reactor, wherein the mixed gas containing methanol from the first synthesis reactor is cooled in heat exchange with either said loop gas or said make-up gas.

U.S. Pat. No. 5,827,901 describes a process in which methanol is produced from a synthesis gas containing hydrogen and carbon oxides on copper-containing catalysts at pressures in the range 20 to 120 bar and temperatures in the range 130 DEG to 350 DEG C. The synthesis gas is first of all passed through a first synthesis reactor, in which the catalyst is provided in tubes surrounded by water as a coolant, which is boiling at an elevated pressure. From the first reactor a first mixture containing gases and methanol vapour is withdrawn and passed without cooling through a second synthesis reactor. In the second reactor the catalyst is cooled with synthesis gas to which a make-up gas has been added.

U.S. Pat. No. 8,629,191 describes a process for producing methanol from a synthesis gas containing hydrogen and carbon oxides wherein the synthesis gas is passed through a first, water-cooled reactor in which a part of the carbon oxides is catalytically converted to methanol. The resulting mixture containing synthesis gas and methanol vapour is supplied to a second, gas-cooled reactor in which a further part of the carbon oxides is converted to methanol. Subsequently, methanol is separated from the synthesis gas, and synthesis gas is recirculated to the first reactor. The cooling gas flows through the second reactor co-current to the mixture withdrawn from the first reactor.

U.S. Pat. No. 5,631,302 describes a process in which methanol is catalytically produced from a synthesis gas containing hydrogen and carbon oxides on copper-containing catalysts under pressures in the range from 20 to 20 bars and at temperatures in the range from 200 to 350 DEG C. The synthesis gas is passed through a first synthesis reactor, which consists of a shaft reactor and contains a fixed bed of a copper-containing catalyst. The reaction in the shaft reactor is carried out adiabatically and without a recycling of synthesis gas. Together with recycle gas, the gas mixture which has not been reacted in the first synthesis reactor is passed through a second synthesis reactor, which contains a copper-containing catalyst, which is disposed in tubes and is indirectly cooled through boiling water.

US 2014/0031438 A1 describes a method for producing methanol from inert-rich syngas by installing a catalytic pre-reactor upstream of a single or multi-stage synthesis loop, a first part of the syngas being converted to methanol in the catalytic pre-reactor. In addition, an inert gas separation stage, for example a pressure swing adsorption system or a membrane system, is connected downstream of the synthesis loop, whereby a hydrogen-enriched syngas stream can be returned to the synthesis loop. In the processing of methane-rich syngas, the inert gas separation stage may also comprise an autothermal reformer in which methane is converted to carbon oxides and hydrogen, which are also returned into the synthesis loop.

WO 2014/012601 A1 describes a process for producing methanol comprising the steps of (a) providing a fresh methanol synthesis gas containing hydrogen, carbon monoxide and carbon dioxide; (b) providing a recycle gas stream containing unconverted methanol synthesis gas and mixing a part of the recycle stream with the fresh synthesis gas to form a process gas stream; (c) introducing and reacting the process gas stream in a first methanol reaction unit in presence of a methanol catalyst and obtaining a first effluent stream containing methanol and a part of the unconverted synthesis gas contained in the recycle stream; and (d) introducing and reacting at least another part of the recycle gas stream in a second methanol reaction unit in presence of a methanol catalyst and obtaining a second effluent stream containing methanol and another part of the unconverted synthesis gas contained in the recycle stream, wherein the recycle stream is pressurised by a common circulator.

WO2014/206635 A1 describes a process for the preparation of methanol in parallel reactors, comprising the steps of (a) reacting carbon oxides and hydrogen in the presence of a methanol catalyst in a first methanol reactor to obtain a first methanol-containing effluent, (b) introducing and reacting unconverted synthesis gas in a second methanol reactor in the presence of a methanol catalyst to obtain a second methanol-containing effluent, the first methanol reactor and the second methanol reactor being connected in parallel, (c) combining the first and second effluent, and (d) cooling and separating the combined and cooled effluent into a methanol-containing liquid phase and unconverted synthesis gas, wherein the methanol catalyst in the first methanol reactor is indirectly cooled by boiling water and the methanol catalyst in the second methanol reactor is either directly or indirectly cooled by the unconverted synthesis gas prior to conversion into the second effluent.

DE 3518362 A1 describes a process for producing methanol where, starting from a conventional methanol synthesis process in which unreacted synthesis gas is recycled to the inlet of the reactor, a methanol synthesis reactor which operates without recycling is arranged upstream of the recycling process.

We have realised that the efficiency of multiple-stage methanol synthesis may be improved by using different recycle ratios for different types of reaction reactor.

Accordingly the invention provides a process for the synthesis of methanol comprising the steps of:
  (i) passing a first synthesis gas mixture comprising a make-up gas through a first synthesis reactor containing a cooled methanol synthesis catalyst to form a first product gas stream,
  (ii) recovering methanol from the first product gas stream thereby forming a first methanol-depleted gas mixture,
  (iii) combining the first methanol-depleted gas mixture with a loop recycle gas stream to form a second synthesis gas mixture,
  (iv) passing the second synthesis gas mixture through a second synthesis reactor containing a cooled methanol synthesis catalyst to form a second product gas stream,
  (v) recovering methanol from the second product gas stream thereby forming a second methanol-depleted gas mixture, and
  (vi) using at least part of the second methanol-depleted gas mixture as the loop recycle gas stream,
wherein the first synthesis reactor has a higher heat transfer per cubic meter of catalyst than the second synthesis reactor, none of the loop recycle gas stream is fed to the first synthesis gas mixture and the recycle ratio of the loop recycle gas stream to form the second synthesis gas mixture is in the range 1.1:1 to 6:1.

The present invention utilises the advantages of each type of reaction reactor, hence it has a no recycle ratio section for the first synthesis reactor and a high recycle ratio section for the second synthesis reactor.

By the term "recycle ratio", we mean the molar flow ratio of the recycled loop gas to the make-up gas that form the synthesis gas mixture fed to the second synthesis reactor. Accordingly the recycle ratio for the second synthesis gas arises from the proportion of the loop gas combined with the first methanol-depleted gas mixture, expressed relative to the make-up gas.

Whereas the recycle ratio of the loop recycle gas stream to form the second synthesis gas mixture may be 1.1:1 to 6:1, it is preferably in the range 1.5:1 to 6:1, more preferably 2:1 to 6:1.

The first synthesis gas comprises a make-up gas. Make-up gas typically comprises hydrogen, carbon monoxide, and/or carbon dioxide. The make-up gas may be generated by the steam reforming of methane or naphtha using established steam reforming processes, including pre-reforming. However the present invention is of particular effectiveness in utilising reactive synthesis gases generated by processes including a step of partial oxidation of a hydrocarbon, biomass or carbonaceous feedstock. By "reactive synthesis gases" we mean a synthesis gas comprising hydrogen, carbon monoxide and carbon dioxide in which the ratio (by volume) of carbon monoxide to carbon dioxide is typically ≥2:1, preferably ≥5:1. Such processes include combined reforming in which a first portion of a hydrocarbon feedstock is subjected to steam reforming and a second portion is subjected to autothermal reforming; and from coal or biomass gasification. Alternatively, off-gases from refineries or other chemical processes comprising principally hydrogen and carbon oxides (mainly as carbon monoxide) may also be used.

The use of more reactive synthesis gas leads to smaller catalyst volumes being used, and the greater net heat of reaction gives a heat release per unit volume of catalyst which can be more than double that in a process based on steam reforming alone. Therefore providing effective cooling of the catalyst becomes more important as the carbon monoxide to carbon dioxide ratio in the synthesis gas increases.

The make-up gas may be passed directly to the first methanol synthesis reactor without dilution with other gases. This may be performed when the make-up gas contains modest amounts of carbon monoxide, for example in the range 10-20% vol CO. Such synthesis gases may be obtained by conventional steam reforming of hydrocarbons. However, if desired the stoichiometry of the first synthesis gas may be adjusted for example by adding a hydrogen-containing gas stream, to optimise methanol synthesis in the first synthesis reactor. This may be particularly the case where the make-up gas contains higher amounts of carbon monoxide, for example in the range 20-35% vol or 25-35% vol. Such reactive synthesis gases may be obtained in particular by the gasification of coal or biomass, or from a hydrocarbon reforming process based on combined reforming or autothermal reforming. In these cases, the first synthesis gas is desirably diluted with a hydrogen-containing gas stream selected from a purge gas stream from other methanol processes or a hydrogen gas stream obtained for example by pressure-swing absorption or by membrane separation from a suitable hydrogen-containing gas mixture.

The composition of first synthesis gas at the first synthesis reactor inlet is preferably as follows; 15-30 mol % carbon monoxide, 0.5-10 mol % carbon dioxide, 55-85 mol % hydrogen and the balance one or more inert gases. The pressure of the first synthesis gas at the first synthesis reactor inlet is preferably 50-100 bar abs. The temperature of the first synthesis gas at the first synthesis reactor inlet is preferably 200-250° C. and at the outlet preferably 230-280° C.

The composition of second synthesis gas at the second synthesis reactor inlet is preferably as follows; 3-10 mol % carbon monoxide, 0.5-10 mol % carbon dioxide, 65-95 mol % hydrogen and the balance one or more inert gases. The pressure of the second synthesis gas at the second synthesis reactor inlet is preferably 50-100 bar abs. The temperature of the second synthesis gas at the second synthesis reactor inlet is preferably 215-250° C. and at the outlet preferably 250-300° C.

A single circulator may be used for feeding the combined loop recycle gas and the first methanol depleted gas mixture to the second synthesis reactor.

In the present invention, at least part of the second methanol-depleted gas mixture is used as the loop recycle gas stream. Accordingly the second methanol-depleted gas is the source of the loop recycle gas stream. A purge stream may be recovered from the second methanol-depleted gas and/or the loop recycle gas stream.

If desired, for example, if shipping diameter is a limitation, in order to adjust the duty and so relative size of the first and second synthesis reactors, a proportion of the make-up gas may bypass the first synthesis reactor and enter the high recycle ratio loop as a secondary feed. Thus a portion of the make-up gas in the range 0-70% vol may be fed to the second synthesis reactor. However, for efficiency reasons, preferably the portion is ≤10% vol of the make-up gas and more preferably 0% vol, i.e. there is no by-pass, so that the process is operated in series.

The first synthesis reactor is preferably a design with a higher heat transfer relative to the cooled catalyst volume. The heat transfer can be conveniently characterised by the Volumetric UA. The Volumetric UA may be defined as the multiple of the overall heat transfer coefficient, U, times the total heat transfer area A, per cubic meter of cooled catalyst in the reactor. Although any converter could be used in this position, desirably the first synthesis reactor has a Volumetric UA of ≥50 kW/m$^3$/K and more preferably ≥90 kW/m$^3$/K. Such converters include those where the catalyst is disposed in a plurality of tubes that are cooled by a heat exchange medium.

The second synthesis reactor has a lower heat transfer relative to the cooled catalyst volume than the first synthesis reactor. For example the Volumetric UA may be ≤40 kW/m$^3$/K. The second synthesis reactor can be of any type, but high overall conversion of carbon oxides into methanol is associated with high recycle flows or low converter exit temperature. There are several converter types that may be used and these include: (i) converters featuring one or more adiabatic beds and with no heat transfer surface in contact with the catalyst (ii) converters with gas cooling, such as a tube cooled converter, an isothermal methanol converter and a gas-cooled converter, and (iii) water-cooled converters with radial flow.

The first and second synthesis reactors may comprise one or more reactors.

In a preferred arrangement, the first synthesis reactor comprises a methanol synthesis catalyst disposed in tubes that are cooled by water under pressure, and the second synthesis reactor comprises a fixed bed of a methanol synthesis catalyst that is cooled in heat exchange with either water under pressure or a synthesis gas mixture selected from the first synthesis gas mixture and the second synthesis gas mixture.

Preferably the first synthesis reactor is an axial-flow, steam-raising converter (aSRC). In such reactors the synthesis gas typically passes axially through vertical, catalyst-containing tubes that are cooled in heat exchange with boiling water under pressure. The catalyst may be provided in pelleted form directly in the tubes or may be provided in one or more cylindrical containers that direct the flow of synthesis gas both radially and axially to enhance heat transfer. Such contained catalysts and their use in methanol synthesis are described in WO2012146904 (A1). An aSRC typically has a Volumetric UA 100 kW/m$^3$/K. Steam raising converters in which the catalyst is present in tubes cooled by boiling water under pressure offer a useful means to remove heat from the catalyst. However, while the aSRC offers the highest cooling factor, it makes poorer use of the reactor volume so the reactor shell is relatively large for the quantity of catalyst that it holds. Furthermore, aSRC's can suffer from a high pressure drop. By having no recycle to the first synthesis reactor the advantages of the aSRC are maximised while the disadvantages are minimised.

The second synthesis reactor may be a radial-flow steam raising converter, a gas-cooled converter or a tube cooled converter. In each of these, a bed of particulate catalyst is cooled by tubes or plates through which a coolant heat exchange medium passes. Alternatively the second synthesis reactor may be a quench reactor in which one or more beds of particulate catalyst are cooled by a synthesis gas mixture injected into the reactor within or between the beds.

In a radial-flow steam raising converter (rSRC) the synthesis gas typically passes radially (inwards or outwards) through a bed of particulate catalyst which is cooled by a plurality of tubes or plates through boiling water under pressure is fed as coolant. Such reactors are known and are described for example in U.S. Pat. No. 4,321,234. A rSRC has poorer heat transfer than an aSRC but has very low pressure drop, hence it favours operation with high recycle ratio. A rSRC typically has a Volumetric UA in the range 12-24 kw/m$^3$/K.

In a tube-cooled converter (TCC), the catalyst bed is cooled by feed synthesis gas passing through open-ended tubes disposed within the bed that discharge the heated gas to the catalyst. TCC's therefore can provide sufficient cooling area for a more reactive synthesis gas e.g. from combined reforming or coal gasification, but the increased heat of reaction would mean that the circulating loop gas flow would be insufficient to carry away the reaction heat unless the recycle ratio is high. A TCC typically has a Volumetric UA in the range 6-15 kW/m$^3$/K. As an alternative to a TCC, a gas cooled converter (GCC), may be used to cool the catalyst bed by passing the synthesis gas though tubes in a heat exchanger-type arrangement. A GCC is described for example in the aforesaid U.S. Pat. No. 5,827,901. The use of a TCC is preferred over the GCC in that it is simpler and cheaper to fabricate due to the use of open topped tubes and the elimination of the upper header and all of the differential expansion problems that the gas cooled converter raises. A TCC therefore has the advantage of low equipment cost and lower outlet temperature, which favours the synthesis reaction equilibrium, but it has a lower heat transfer than aSRC and higher pressure drop than rSRC.

In a quench reactor, the one or more beds of particulate catalyst are cooled by a synthesis gas mixture injected into the reactor within or between the beds. Accordingly, a quench reactor has a Volumetric UA of 0 kW/m$^3$/K. Such reactors are described, for example, in U.S. Pat. Nos. 3,458,289, 3,475,136 and 4,411,877.

Alternative converter designs, such as the Linde Variobar converter comprising a bed of methanol synthesis catalyst cooled in heat exchange with boiling water passing through a spiral-wound heat exchanger within the bed, typically have an intermediate Volumetric UA of 30-40 kW/m$^3$/K. Such converters may be used as the second synthesis reactor in combination, for example, with an axial-flow steam-raising converter, or may be used as the first synthesis reactor in combination with a quench reactor, a tube-cooled converter or even a radial-flow steam-raising converter.

The methanol synthesis catalysts are preferably copper-containing methanol synthesis catalysts, in particular the methanol synthesis catalyst in the first and second synthesis reactors is a particulate copper/zinc oxide/alumina catalyst. Particularly suitable catalysts are Mg-doped copper/zinc oxide/alumina catalysts as described in U.S. Pat. No. 4,788,175. The same or different methanol synthesis catalysts may be used in the first and second synthesis reactors.

Methanol synthesis may be effected in the first and second synthesis reactors conventionally at elevated temperature and pressure, for example pressures in the range 20 to 120 bar abs and temperatures in the range 130° C. to 350° C. Where two-stage or separate circulation is effected for the recycle loop gas to the first and second synthesis reactors, they may be operated at the same or different pressures. Thus the first reactor may be operated at a higher pressure, the same pressure or a lower pressure than the second reactor. This may provide advantages in methanol recovery. In a preferred embodiment, the pressure in the second synthesis reactor is higher than the pressure in the first synthesis reactor. The difference in pressure between the reactors may be bar. The circulators may be conventional compressors suitably adapted for processing the recycle loop gas at the desired pressures.

The product gas stream withdrawn from the second synthesis reactor typically has temperatures in the range from 180 to 250° C.

The proportion of the methanol made in the first and second reactors may be in the range 30:70 to 70:30, for example 40:60 to 60:40 or 50:50.

The gas mixtures fed to the first and second synthesis reactors may be heated before being fed to the reactors. The heating may be effected by conventional heat exchange using a suitable heat exchange apparatus. Preferably, the first and second synthesis gases are heated in gas-gas heat exchangers using the product gases from the reactors. Other temperature adjustment of the feed or product gases may be performed using conventional heat exchange apparatus. Thus the product gas streams from the first and second synthesis reactors may be cooled in one or more stages of heat exchange, e.g. with water or air cooling, to condense methanol therefrom, which may suitably be recovered using gas-liquid separators. The cooling may be performed to fully or partially condense the methanol from the first and second product gas streams. Preferably all the methanol is condensed from the second product gas stream. The recovered liquid methanol streams may be processed separately but are preferably combined and passed for further processing, such as one or more, preferably two or three, stages of distillation to produce a purified methanol product.

A purge gas stream is preferably recovered from the loop to avoid the build-up of inert gases, such as nitrogen, methane and argon in the loop. The purge gas typically comprises hydrogen and carbon oxides and may be used for hydrogen recovery, for example by pressure-swing absorption or by using suitable membranes, or may be subjected to one or more further processing stages including autothermal reforming, water-gas shift and methanol synthesis. The purge may be recovered from the first methanol-depleted gas or the second methanol depleted gas depending on whether the stoichiometry of the make-up gas is hydrogen-rich or carbon-rich. Preferably the purge is recovered from the second methanol depleted gas mixture and the remaining methanol depleted gas mixture used as the recycle loop gas mixture.

The invention will be further described by reference to the FIGURE in which;

FIG. 1 depicts a process according to one embodiment of the present invention utilising an aSRC and rSRC.

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

In FIG. 1, a make-up gas in line 10 comprising hydrogen, carbon monoxide and carbon dioxide is optionally combined with a hydrogen-containing gas fed by dotted-line 12 and the resulting first synthesis gas mixture passed via line 14 to a gas-gas interchanger 16 where it is heated in indirect heat exchange with a first product gas stream 24. The heated first synthesis gas mixture is fed by line 18 to the inlet of an axial steam-raising converter 20, containing catalyst-filled tubes 22 through which the synthesis gas mixture is passed. The tubes are cooled by boiling water under pressure. The catalyst is a particulate copper/zinc oxide/alumina catalyst. The boiling water under pressure is fed to the shell side of the reactor and a mixture of boiling water and steam is withdrawn and supplied to a steam drum (not shown). The methanol synthesis reaction takes place as the synthesis gas passes axially through the catalyst-filled tubes 22 to form a first product gas stream containing methanol vapour. The first product gas stream is recovered from the outlet of the first synthesis reactor 20 and fed via line 24 to the interchanger 16 where it is partially cooled. The partially cooled gas is fed via line 26 to one or more further stages of heat exchange 28 to condense methanol therefrom. The resulting gas-liquid mixture is passed to a gas-liquid separator 30 and liquid methanol is recovered via line 32. A first methanol-depleted gas mixture comprising unreacted hydrogen and carbon oxides is recovered from the separator 30 and fed by line 34 to a recycle loop where is combined with a portion of a second methanol-depleted gas fed by line 36 to form a second synthesis gas mixture. The second synthesis gas mixture is passed by line 38 to a circulator 40. The circulator compresses the second synthesis gas mixture, which is fed from the circulator by line 42 to a gas-gas interchanger 44 where it is heated in indirect heat exchange with a second product gas stream 52. The heated second synthesis gas is fed by line 46 to the inlet of a radial steam-raising converter 48 containing a bed of methanol synthesis catalyst 50, containing a plurality of heat exchange tubes though which boiling water under pressure is passed as coolant. Whereas tubes are depicted, alternative heat exchange devices such as plates through which the coolant may be passed, may also be used. The catalyst is a particulate copper/zinc oxide/alumina catalyst. The boiling water under pressure is fed to the tube side of the reactor and a mixture of boiling water and steam is withdrawn and supplied to a steam drum (not shown). The methanol synthesis reaction takes place as the synthesis gas passes radially through the bed of catalyst 50 to form a second product gas stream containing methanol vapour. The second product gas stream is recovered from the outlet of the second synthesis reactor 48 and fed via line 52 to the interchanger 44 where it is partially cooled. The partially cooled gas is fed via line 54 to one or more further stages of heat exchange 56 to condense methanol therefrom. The resulting gas liquid mixture is passed to a gas-liquid separator 58 and liquid methanol is recovered via line 64. A second methanol-depleted gas mixture is recovered in the separator 58 and fed by line 60 to a purge off-take line 62, which removes a portion of the gas to reduce the build-up of inert gases. The remaining second methanol-depleted gas mixture is fed to the recycle loop line 36 where is combined with the unreacted gas fed by line 34. The crude methanol streams 32 and 64 are combined and send by line 66 for further processing such as one or more stages of distillation to produce a purified methanol product.

The invention will further be described by reference to the following Example.

A flowsheet was modelled to illustrate the composition and flow of the various gas streams in a process as depicted in FIG. 1, in which the radial steam-raising converter 48 was replaced with a tube cooled converter. The compositions, temperatures and pressures are set out in the following tables.

| Stream | 10 | 12 | 14 | 18 | 24 | 32 | 34 |
|---|---|---|---|---|---|---|---|
| Pressure MPa(abs) | 8.5 | 8.5 | 8.5 | 8.2 | 8.0 | 7.7 | 7.7 |
| Temperature ° C. | 150 | 40 | 132 | 230 | 258 | 50 | 50 |
| Flow kNm³/hr (vapour) | 465 | 91 | 556 | 556 | 427 |  | 358 |
| Flow Tonne/hr (liquid) |  |  |  |  |  | 96.6 |  |
| Composition Mole % |  |  |  |  |  |  |  |
| $H_2O$ | 0.5 | 0.1 | 0.4 | 0.4 | 0.9 | 5.7 | 0.0 |
| $H_2$ | 65.8 | 82.0 | 68.5 | 68.5 | 58.5 | 0.4 | 69.7 |
| CO | 22.7 | 3.1 | 19.4 | 19.4 | 10.6 | 0.4 | 12.5 |
| $CO_2$ | 8.7 | 3.2 | 7.8 | 7.8 | 9.7 | 3.2 | 11.0 |
| $CH_3OH$ | 0 | 0.4 | 0.1 | 0.1 | 15.2 | 89.8 | 0.9 |
| Inerts | 2.4 | 11.3 | 3.8 | 3.8 | 5.0 | 0.3 | 5.9 |

| Stream | 36 | 42 | 46 | 52 | 60 | 62 | 64 |
|---|---|---|---|---|---|---|---|
| Pressure MPa(abs) | 7.6 | 8.3 | 8.2 | 8.0 | 7.7 | 7.6 | 7.7 |
| Temperature ° C. | 50 | 59 | 153 | 241 | 50 | 50 | 50 |
| Flow kNm³/hr (vapour) | 1838 | 2196 | 2196 | 2040 | 1921 | 83 |  |
| Flow Tonne/hr (liquid) |  |  |  |  |  |  | 146.5 |
| Composition Mole % |  |  |  |  |  |  |  |
| $H_2O$ | 0.1 | 0.1 | 0.1 | 1.8 | 0.1 | 0.1 | 29.8 |
| $H_2$ | 69.3 | 69.3 | 69.3 | 65.3 | 69.3 | 69.3 | 0.2 |
| CO | 2.3 | 3.9 | 3.9 | 2.1 | 2.3 | 2.3 | 0.0 |
| $CO_2$ | 3.8 | 5.0 | 5.0 | 3.7 | 3.8 | 3.8 | 0.8 |
| $CH_3OH$ | 0.7 | 0.7 | 0.7 | 4.6 | 0.7 | 0.7 | 68.1 |
| Inerts | 23.8 | 20.9 | 20.9 | 22.5 | 23.8 | 23.8 | 0.9 |

As in FIG. 1, the first synthesis reactor (the axial steam raising converter 20) has a higher heat transfer per cubic meter of catalyst than the second synthesis reactor (the tube-cooled converter), none of the loop recycle gas stream is fed to the first synthesis gas mixture and the recycle ratio of the loop recycle gas stream to form the second synthesis gas mixture is in the range 1.1:1 to 6:1.

The invention claimed is:

1. A process for synthesizing methanol comprising the steps of:
   (i) passing a first synthesis gas mixture comprising a make-up gas through a first synthesis reactor containing a first cooled methanol synthesis catalyst to form a first product gas stream,
   (ii) recovering methanol from the first product gas stream to form a first methanol-depleted gas mixture,
   (iii) combining the first methanol-depleted gas mixture with a loop recycle gas stream to form a second synthesis gas mixture,
   (iv) passing the second synthesis gas mixture through a second synthesis reactor containing a second cooled methanol synthesis catalyst to form a second product gas stream,
   (v) recovering methanol from the second product gas stream to form a second methanol-depleted gas mixture, and
   (vi) using at least part of the second methanol-depleted gas mixture as the loop recycle gas stream,
   wherein the first synthesis reactor has a higher heat transfer per cubic meter of catalyst than the second synthesis reactor, none of the loop recycle gas stream is fed to the first synthesis gas mixture and the recycle ratio of the loop recycle gas stream to form the second synthesis gas mixture is in the range of from 1.1:1 to 6:1.

2. The process according to claim 1 wherein the make-up gas contains carbon monoxide in the range of from 10-20% vol and is passed directly to the first cooled methanol synthesis reactor without diluting with other gases.

3. The process according to claim 1 wherein the make-up gas contains carbon monoxide in the range of from 20-35% vol and is diluted with a hydrogen-containing gas stream selected from a purge gas stream from another methanol process or a hydrogen gas stream.

4. The process according to claim 1 wherein a single circulator is used for feeding the combined loop recycle gas and the first methanol depleted gas mixture to the second synthesis reactor.

5. The process according to claim 1 wherein the recycle ratio of the loop recycle gas stream to form the second synthesis gas mixture is in the range of from 1.5:1 to 6:1.

6. The process according to claim 1 wherein the first synthesis reactor comprises a first cooled methanol synthesis catalyst disposed in tubes that are cooled by water under pressure, the second synthesis reactor comprises a fixed bed of a second cooled methanol synthesis catalyst that is cooled in heat exchange with either water under pressure or a synthesis gas mixture from the first synthesis gas mixture or the second synthesis gas mixture.

7. The process according to claim 1 wherein the first synthesis reactor is axial flow steam-raising converter.

8. The process according to claim 1 wherein the second synthesis reactor is selected from a radial flow steam-raising converter, a tube-cooled converter, a gas-cooled converter or a quench reactor.

9. The process according to claim 1, wherein the first, second, or first and second cooled methanol synthesis catalyst is a copper-containing methanol synthesis catalyst.

10. The process according to claim 1 wherein methanol synthesis in the first and second reactors is performed at pressures in the range of from 20 to 120 bar abs and temperatures in the range of from 130° C. to 350° C.

11. The process according to claim 1 wherein the gas mixtures fed to the first and second synthesis reactors are heated in gas-gas heat exchangers using the product gases from the reactors.

12. The process according to claim 1 wherein the product gas streams from the first and second synthesis reactors are cooled in one or more stages of heat exchange to condense methanol therefrom.

13. The process according to claim 1 wherein a purge gas stream is recovered from the second methanol depleted gas mixture and is used for hydrogen recovery, or is subjected to one or more further processing stages including autothermal reforming, water-gas shift, or methanol synthesis.

14. The process according to claim 1 wherein the recycle ratio of the loop recycle gas stream to form the second synthesis gas mixture is in the range of from 2:1 to 6:1.

15. The process according to claim 1 wherein the first, second, or first and second cooled methanol synthesis catalyst is a compositions comprising copper, zinc oxide and alumina.

16. The process according to claim 12, wherein the condensed methanol is recovered and further processed using one or more stages of distillation to produce a purified methanol product.

* * * * *